(12) United States Patent
Shinano et al.

(10) Patent No.: US 7,001,647 B2
(45) Date of Patent: Feb. 21, 2006

(54) PERFLUOROALLYLOXY COMPOUND AND LIQUID CRYSTAL COMPOSITION CONTAINING THE SAME

(75) Inventors: Hirokatsu Shinano, Saitama (JP); Takahiro Otsuka, Saitama (JP); Masatomi Irisawa, Saitama (JP)

(73) Assignee: Asahi Denka Co., Ltd., Tokyo (JP)

( * ) Notice: Subject to any disclaimer, the term of this patent is extended or adjusted under 35 U.S.C. 154(b) by 85 days.

(21) Appl. No.: 10/505,080

(22) PCT Filed: Dec. 4, 2003

(86) PCT No.: PCT/JP03/15547

§ 371 (c)(1),
(2), (4) Date: Aug. 20, 2004

(87) PCT Pub. No.: WO2004/058676

PCT Pub. Date: Jul. 15, 2004

(65) Prior Publication Data

US 2005/0161637 A1  Jul. 28, 2005

(30) Foreign Application Priority Data

Dec. 24, 2002  (JP) ............... 2002-372303
Jan. 16, 2003  (JP) ............... 2003-8467 U

(51) Int. Cl.
C09K 19/30 (2006.01)
C09K 19/12 (2006.01)
C09K 19/20 (2006.01)
C09K 19/34 (2006.01)
C07C 43/172 (2006.01)

(52) U.S. Cl. ............ 428/1.1; 252/299.61; 252/299.63; 252/299.65; 252/299.66; 252/299.67; 544/335; 549/369; 570/136

(58) Field of Classification Search ............... 428/1.1; 252/299.61, 299.63, 299.65, 299.66, 299.67; 570/136; 544/335; 549/369

See application file for complete search history.

(56) References Cited

U.S. PATENT DOCUMENTS

| 4,273,728 A | * | 6/1981 | Krespan ............... 558/449 |
| 4,330,426 A | | 5/1982 | Eidenschink et al. |
| 4,617,140 A | | 10/1986 | Eidenschink et al. |
| 5,122,295 A | | 6/1992 | Weber et al. |
| 5,196,140 A | | 3/1993 | Poetsch et al. |
| 5,403,512 A | | 4/1995 | Bartmann et al. |

FOREIGN PATENT DOCUMENTS

| DE | 42 23 501 | 1/1994 |
| EP | 0 062 324 | 10/1982 |
| JP | 55-040660 | 3/1980 |
| JP | 55-072143 | 5/1980 |
| JP | 58-177939 | 10/1983 |
| JP | 58-210045 | 12/1983 |
| JP | 59-078129 | 5/1984 |
| JP | 61-197563 | 9/1986 |
| JP | 4-312 546 | 11/1992 |
| JP | 10-067989 | 3/1998 |

* cited by examiner

Primary Examiner—Shean C. Wu
(74) Attorney, Agent, or Firm—Young & Thompson

(57) ABSTRACT

A novel perfluoroallyloxy compound represented by general formula (I) and a liquid crystal composition containing the compound are disclosed. The perfluoroallyloxy compound is useful as a liquid crystal material (I)

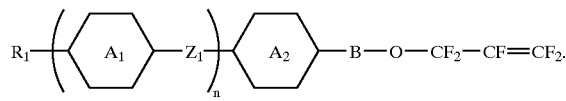

9 Claims, No Drawings

PERFLUOROALLYLOXY COMPOUND AND LIQUID CRYSTAL COMPOSITION CONTAINING THE SAME

TECHNICAL FIELD

The present invention relates to a novel perfluoroallyloxy compound and a liquid crystal composition containing the same. The perfluoroallyloxy compound of the invention is useful as a liquid crystal material.

BACKGROUND ART

A large number of liquid crystal displays (LCDs) utilizing optical (refractive index) anisotropy (Δn) (hereinafter sometimes simply referred to as Δn) and dielectric anisotropy (Δε) (hereinafter sometimes simply referred to as Δε) characteristic of a liquid crystal compound have been produced. LCDs have been widely applied to watches, calculators, various measuring instruments, automotive panels, word processors, electronic notebooks, mobile phones, printers, computers, TV sets, etc. with demand increasing year by year. A liquid crystal compound exhibits an inherent liquid crystal phase between a solid phase and a liquid phase. The liquid crystal phase is roughly classified into a nematic phase, a smectic phase, and a cholesteric phase. For display applications, a nematic phase is most widely used. Number of display modes have been proposed for LCD application, including dynamic scatter (DS), guest host (GH), twist nematic (TN), super twist nematic (STN), thin film transistor (TFT), and ferroelectric liquid crystal (FLC). Drive systems known for LCD application include static drive, time division drive, active matrix drive, and dual frequency drive.

It is known that the threshold voltage of an electric field effect type LCD using a liquid crystal composition having a positive dielectric anisotropy Δε is in general inversely proportional to the square root of the Δε. In recent years, a liquid crystal material with a decreased threshold value has been demanded particularly for application to twist nematic (TN) mode LCDs that have now mostly come to adopt a battery drive system. To meet the demand, a liquid crystal material with a large positive Δε is of importance.

Having a large Δε, nitrile compounds including a 4-(p-alkylcyclohexyl)benzonitrile have been employed as a liquid crystal material for TN mode LCDs or super twist nematic (STN) mode LCDs. However, because these nitrile compounds are liable to entrap ionic impurities, they are inapplicable to active matrix drives requiring high resistivities ($10^{12}$ Ωcm or higher). Therefore, a liquid crystal material with high resistivity and large Δε has been awaited.

The viscosity of a liquid crystal composition influences the response time of LCDs. The lower the viscosity, the shorter the response time. Accordingly, it is desirable for the components compounded into a liquid crystal compositions to have low viscosities.

The refractive index anisotropy exerts large influence on visual characteristics of LCDs. The contrast increases with an increase of refractive index anisotropy, and the viewing angle widens with a decrease of the anisotropy. In recent years there is a trend toward liquid crystal materials with a small Δn, namely a wide viewing angle.

An NI point governs the temperature range in which a liquid crystal material shows a liquid crystal state. A liquid crystal material having a higher NI point exhibits a liquid crystal state at a higher temperature.

Compounds terminated with a fluoroalkyl(oxy) group exhibit positive dielectric anisotropy and hardly entrap ionic impurities. They are known as liquid crystal materials capable of developing characteristics required particularly of active matrix drive systems, such as high resistivity, high voltage holding ratio (VHR), and a low ion density. Many compounds having a fluoroalkyl(oxy) group introduced therein have hitherto been proposed. For example, JP-A-55-72143, JP-A-55-40660, JP-A-61197563, JP-A-56-12322, JP-A-58-154532, JP-A-58-177939, JP-A-58-210045, JP-A-5978129, and JP-T-6-500343 propose various kinds of fluoroalkyl-containing compounds. JP-T-1-503145 discloses an electro-optical display device using a compound containing a fluoroalkyl group. JP-T-3-502942 proposes an active matrix LCD using a compound having a fluoroalkyl(oxy) group.

Nevertheless, the fluoroalkyl-containing compounds specifically described in these publications are still unsatisfactory in terms of the demand for low viscosity and a broader temperature range for a nematic phase.

DISCLOSURE OF THE INVENTION

An object of the present invention is to provide a novel liquid crystal material that can be mixed with a nematic liquid crystal material to provide a liquid crystal composition having a low viscosity, a low refractive index anisotropy (Δn), a high dielectric anisotropy (Δε), and a high NI point (i.e., broad nematic phase range).

As a result of extensive investigations, the present inventors have found that the above object of the invention is accomplished by a perfluoroallyloxy compound.

Based on the above finding, the present invention provides a perfluoroallyloxy compound represented by general formula (I) shown below and a liquid crystal composition containing the compound.

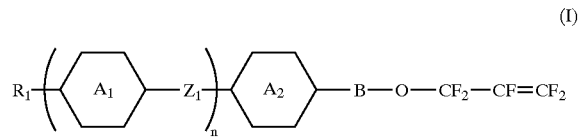

(I)

wherein $R_1$ represents R, RO, ROCO or RCOO; R represents an alkyl group which may have an unsaturated bond, a —$CH_2$— moiety of which may be displaced with —O—, —CO— or —COO—, and a part or all of the hydrogen atoms of which may be substituted with a halogen atom or a cyano group; $A_1$ and $A_2$ each represent 1,4-phenylene (a —CH= moiety of which may be displaced with —N=, and a part or all of the hydrogen atoms of which may be substituted with a halogen atom or a cyano group), 1,4-cyclohexylene (a —$CH_2$— moiety of which may be displaced with —O— or —S—, and a part or all of the hydrogen atoms of which may be substituted with a halogen atom or a cyano group), 2,6-naphthylene or 2,6-decahydronaphthylene; $Z_1$ represents a single bond, —COO—, —OCO—, —$CH_2CH_2$—, —CH=CH—, —$(CH_2)_4$—, —$CH_2O$—, —$OCH_2$—, —$(CH_2)_3O$—, —$O(CH_2)_3$—, —CH=$CHCH_2O$—, —$OCH_2$CH=CH—, —C≡C—, —$CF_2O$— or —$OCF_2$—; B represents a single bond or an alkylene group a part of the hydrogen atom of which may be substituted with a halogen atom or a cyano group; and n represents a number of 1 to 3; when n is 2 or 3, $A_1$'s and $Z_1$'s may each be the same or different.

BEST MODE FOR CARRYING OUT THE INVENTION

In general formula (I) representing the perfluoroallyloxy compound of the present invention, $R_1$ represents R, RO, ROCO or RCOO. The alkyl group represented by R includes methyl, ethyl, propyl, butyl, pentyl, hexyl, heptyl, octyl, nonyl, decyl, vinyl, allyl, butenyl, ethynyl, propynyl, butynyl, methoxymethyl, ethoxymethyl, propoxymethyl, butoxymethyl, methoxyethyl, ethoxyethyl, perfluoromethyl, perfluoroethyl, perfluoropropyl, monofluoromethyl, difluoromethyl, 2,2,2-trifluoromethyl, perfluorovinyl, perfluoroallyl, isopropyl, 1-methylpropyl, 2-methylpropyl, 2-butylmethyl, 3-methylbutyl, 2-methylpentyl, 3-methylpentyl, 2-ethylhexyl, 2-propylpentyl, and 1-methylpentyl. $R_1$ is preferably an unsubstituted alkyl group, an unsubstituted alkenyl group or a group —O—$CF_2CF=CF_2$.

The following is a list of structures of the moiety —$(A_1-Z_1)_n$—$A_2$— in general formula (I). Note that the perfluoroallyloxy compounds of the invention are not limited by the list.

—CY—CY—
—CY—PH—
—PH—PH—
—CY—PH3F—
—CY—PH3,5—diF—
—CY—PH2,3—diF—
—CY—CY—CY—
—CY—CY—PH—
—CY—PH—PH—
—PH—PH—PH—
—CY—CY—PH3F—
—CY—CY—PH3,5—diF—
—CY—CY—PH2,3—diF—
—CY—PH3F—PH—
—CY—PH3,5—diF—PH—
—CY—PH2,3—diF—PH—
—CY—PH—PH—CY—
—PH—$CH_2CH_2$—CY—CY—
—CY—PH—$CH_2CH_2$—PH—
—CY—CY—$CH_2CH_2$—PH—
—CY—$CH_2CH_2$—CY—
—PH—$CH_2CH_2$—CY—
—PH—C≡C—PH—
—CY—PH—C≡C—PH—
—PH—COO—PH—
—CY—COO—PH—
—CY—CY—COO—PH—
—PH—COO—PH—PH—
-Pym-PH—
-Dio-PH—
—PH-Pym-
—PH-Dio-
—PH-Pyr-
—PH—$CF_2O$—PH—
—PH—$CH_2O$—PH—
—PH—CH=$CHCH_2O$—PH—
—PH—$(CH_2)_3O$—PH—
—CY—COO-Nap-
—CY—COO-DHN-

The abbreviations used in the above list stand for the following cyclic structures.

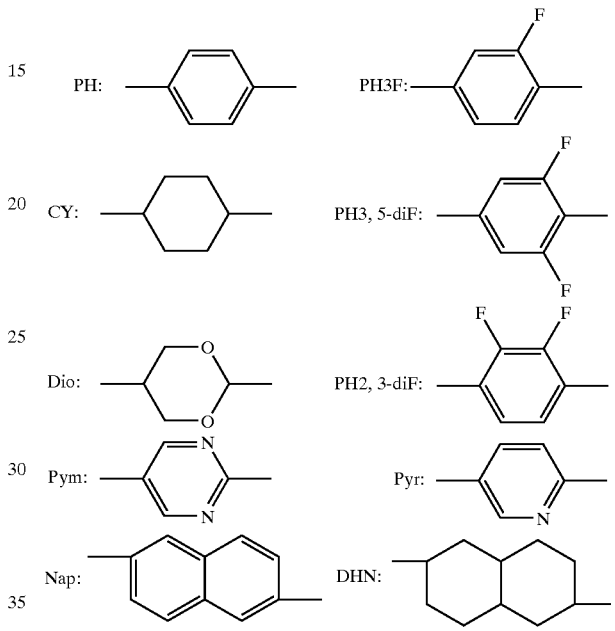

In general formula (I), $A_1$ and $A_2$ each preferably represent an unsubstituted 1,4-phenylene group or an unsubstituted 1,4-cyclohexylene group, or at least one of $A_1$ and $A_2$ is preferably a 1,4-phenylene group substituted with one or two fluorine atoms. $Z_1$ is preferably a single bond or —$CF_2O$—.

The alkylene group represented by B in general formula (I) includes methylene, ethylene, monofluoromethylene, monofluoroethylene, 1,2-difluoroethylene, and 1,1,2-trifluoroethylene.

Specific examples of preferred perfluoroallyloxy compounds represented by general formula (I) include, but are not limited to, compound Nos. 1 through 21 shown below. In compound Nos. 1 to 21, $R_1$ is as defined in general formula (I).

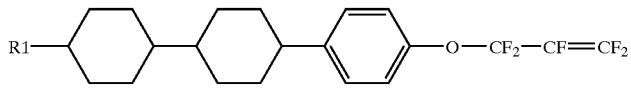

Compound No.1

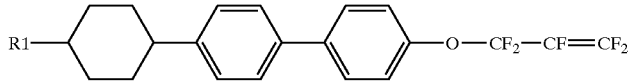

Compound No.2

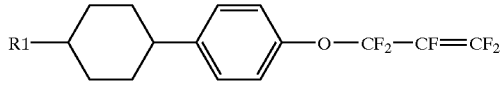

Compound No.3

-continued
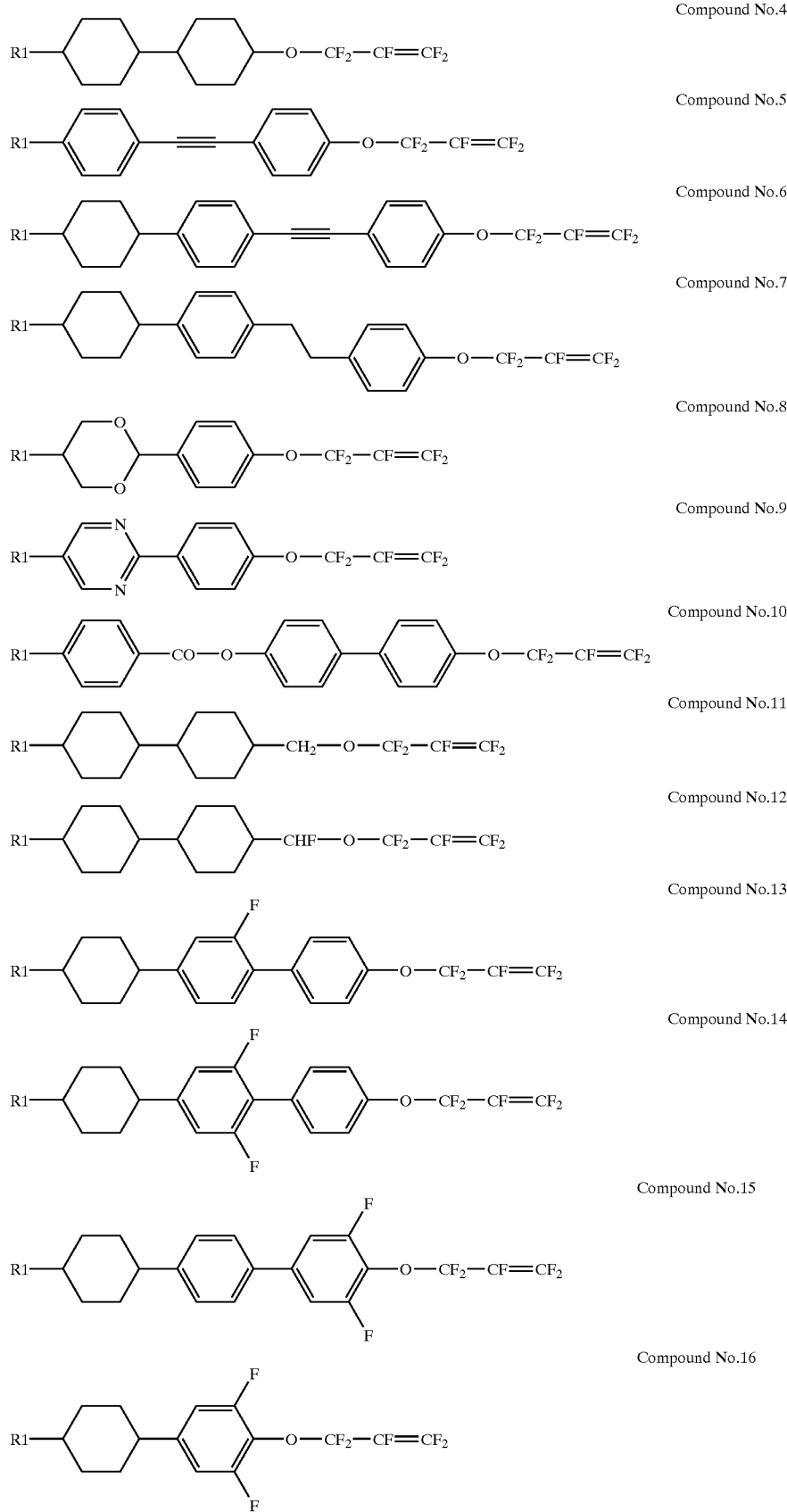

-continued

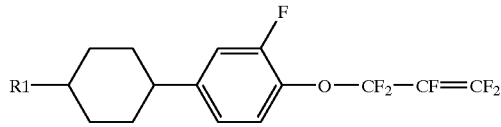
Compound No.16

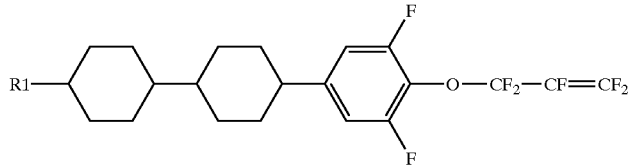
Compound No.18

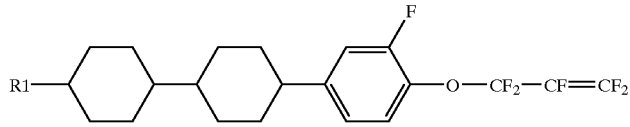
Compound No.19

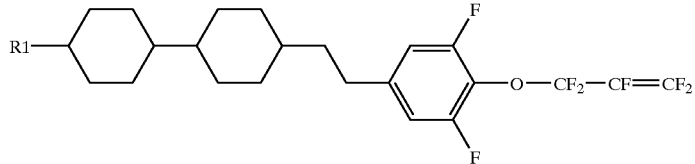
Compound No.20

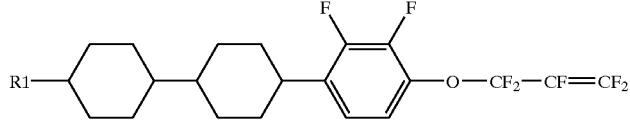
Compound No.21

Of the perfluoroallyloxy compounds of the present invention, those composed of an unsubstituted benzene ring and/or an unsubstituted cyclohexane ring (e.g., compound Nos. 1 to 4, 11, and 12) have a low viscosity and a high NI point; and those having a benzene ring substituted with a fluorine atom at a lateral position thereof (e.g., compound Nos. 13 to 21) are useful for their broad liquid crystal phase range. In particular, those having a benzene ring substituted with a fluorine atom at both the 2- and 3-positions (e.g., compound No. 21) have a negative Δε and are therefore useful as a material of vertical alignment type or guest-host type electro-optical devices. The other compounds have various advantageous characteristics as well.

The process of producing the perfluoroallyloxy compound of the present invention is not particularly restricted. For example, the compound can be prepared according to the following reaction scheme:

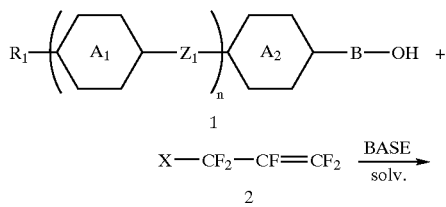

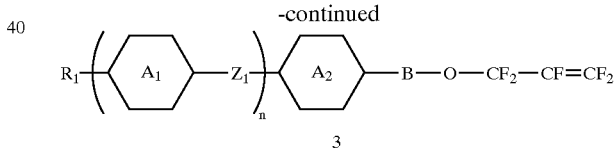

wherein $R_1$, $A_1$, $A_2$, $Z_1$, n, and B are as defined in general formula (I); X represents a halogen atom or $FSO_2O—$; BASE represents a base; and solv. represents a solvent.

The base that can be used in the reaction includes metal hydroxides, such as sodium hydroxide and potassium hydroxide; metal hydrides, such as lithium hydride and sodium hydride; and amines, such as triethylamine, ethyldimethylamine, propyldimethylamine, N,N'-dimethylpiperazine, pyridine, picoline 1,8-diazabicyclo(5.4.0)undecene-1 (DBU), benzyldimethylamine, 2-(dimethylaminoethyl) phenol (DMP-10), and 2,4,6-tris(dimethylaminomethyl)phenol (DMP-30).

In carrying out such etherification as represented by the reaction scheme shown above, Williamson's method is widely used, in which a sodium alkoxide (or phenoxide) prepared from an alcohol compound (or phenol compound) and sodium hydroxide, etc. is allowed to react with an alkyl halide. In the present invention, however, the desired compound is preferably prepared by allowing a phenol compound and a halide or fluorosulfite of perfluoropropene to react in the presence of an amine compound, especially a tertiary amine, such as triethylamine, which achieves a high conversion. The reaction temperature and the reaction time are selected appropriately from a range of −80° to 80° C. and a range of 0 to 20 hours, respectively.

The solvent that can be used in the reaction includes polar solvents, such as dimethylimidazoline, tetrahydrofuran, dimethylformamide, diethyl ether, and dimethylsulfone, and low polarity solvents, such as toluene and ethyl acetate.

In the process according to the reaction scheme shown above, the hydroxy compound (1) and the perfluoro compound (2) are preferably used at a (1)/(2) mass ratio of 20/1 to 1/20, still preferably 1/1 to 1/10.

The base is preferably used in an amount of 0.1 to 5.0 equivalents, still preferably 1.0 to 2.0 equivalents, based on 1 equivalent of the hydroxy compound (1).

The amount of the solvent to be used preferably ranges, but is not limited to, 10 to 500 parts by mass per 100 parts of the total of the hydroxy compound (1) and the perfluoro compound (2).

The perfluoroallyloxy compound of the present invention is compounded with a known liquid crystal compound or a liquid crystal-like compound or a mixture thereof as a mother liquid crystal to provide a liquid crystal composition according to the invention. The liquid crystal composition of the invention may consist of the perfluoroallyloxy compound(s) alone.

The mother liquid crystal includes compounds represented by general formula (II) shown below and a mixture thereof.

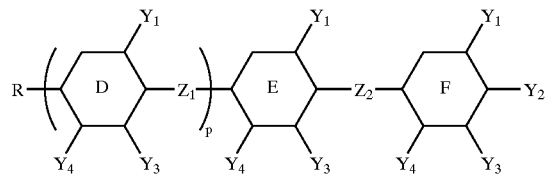

(II)

wherein R represents a hydrogen atom, or such groups having 1 to 8 carbon atoms as an alkyl group, an alkoxy group, an alkenyl group, an alkenyloxy group, an alkynyl group, an alkynyloxy group, an alkoxyalkyl group, an alkanoyloxy group and an alkoxycarbonyl group, wherein those groups may be substituted with a halogen atom, a cyano group, etc.; $Y_2$ represents a cyano group, a halogen atom or a group represented by R; $Y_1$, $Y_3$, and $Y_4$ each represent a hydrogen atom, a halogen atom or a cyano group; $Z_1$ and $Z_2$ each represent a single bond, —CO—O—, —O—CO—, —CH$_2$O—, —OCH$_2$—, —CH$_2$CH$_2$—, —CH═CHCH$_2$O—, —CF$_2$O—, —OCF$_2$— or —C≡C—; p represents 0, 1 or 2; ring D, ring E, and ring F each represent a benzene ring, a cyclohexane ring, a cyclohexene ring, a pyrimidine ring or a dioxane ring.

Specific examples of the compounds represented by general formula (II) are shown below. In the formulae, R, $Y_1$, $Y_2$, $Y_3$, and $Y_4$ are as defined in general formula (II).

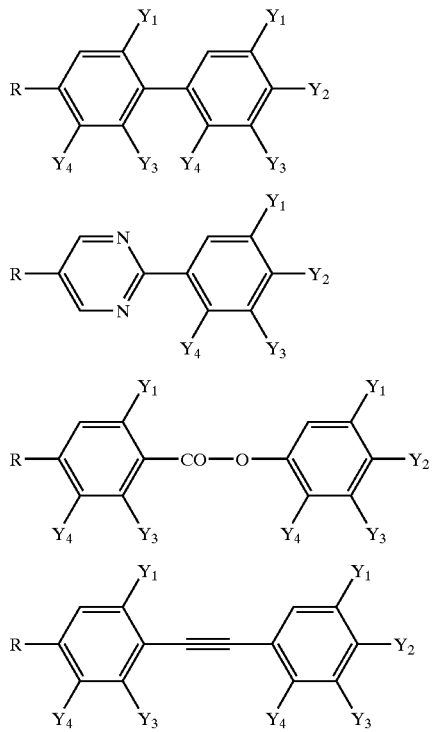
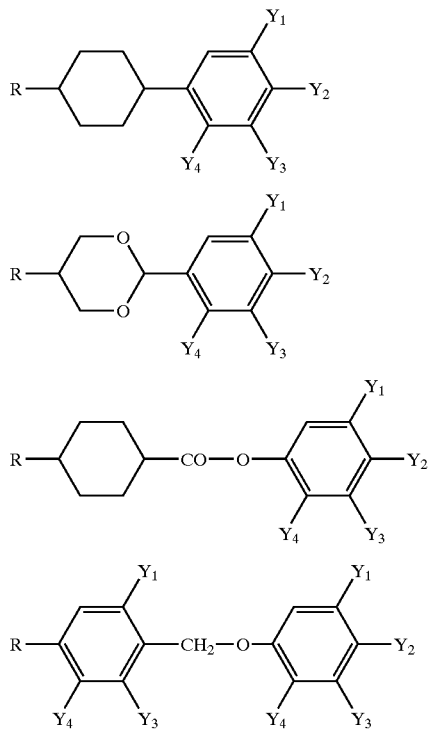

-continued
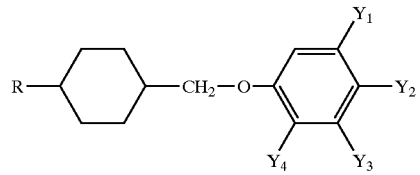
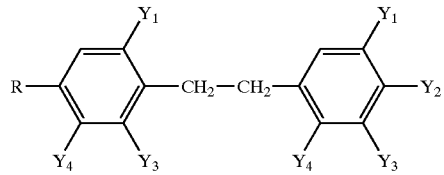
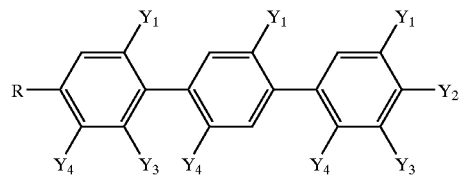
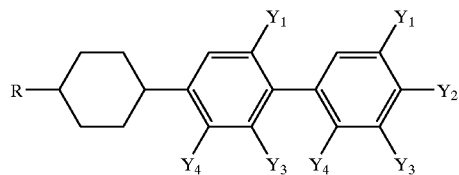
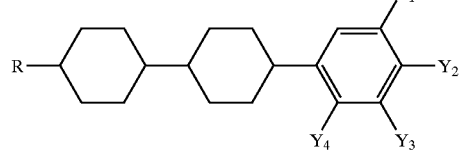
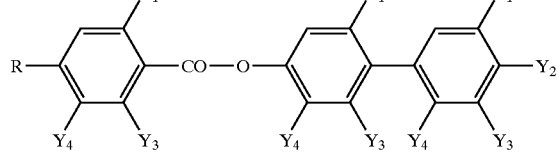
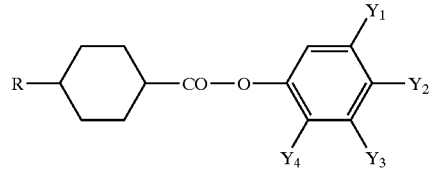
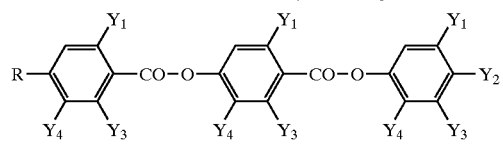
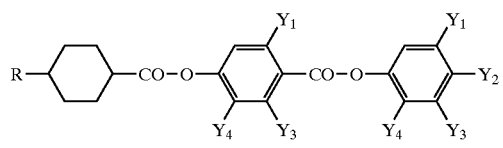
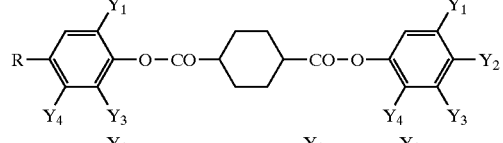
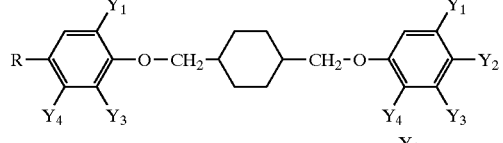
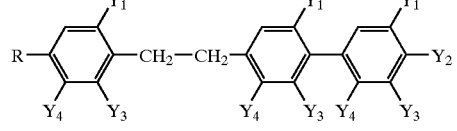
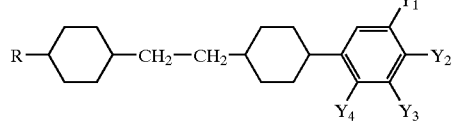
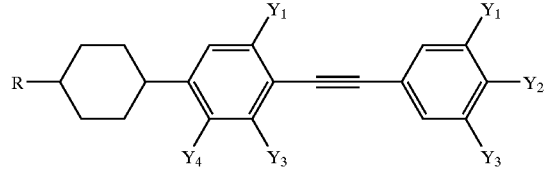
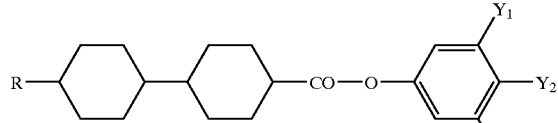
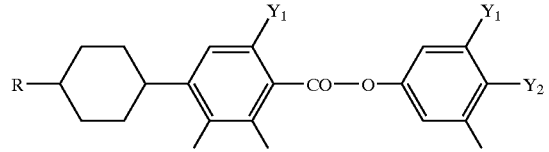
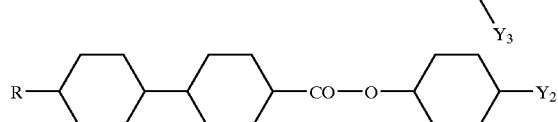
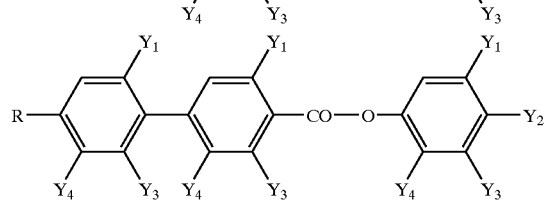
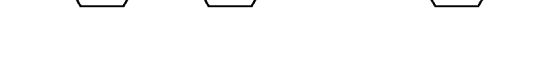

The amount of the perfluoroallyloxy compound of the invention in the liquid crystal composition according to the invention is not particularly limited and is selected appropriately so as to secure desired characteristics. For example, the amount is preferably selected from the range 1 to 100% by mass, still preferably 5 to 90% by mass.

The liquid crystal composition containing the perfluoroallyloxy compound of the present invention can be sealed in a liquid crystal cell to constitute various types of electro-optical display devices. The liquid crystal composition of the present invention is applicable to various types of elector-optical display devices including dynamic scatter (DS) mode, guest-host (GH) mode, twist nematic (TN) mode, super twist nematic (STN) mode, thin film transistor (TFT) mode, thin film diode (TFD) mode, ferroelectric liquid crystal (FLC) mode, anti-ferroelectric liquid crystal (AFLC) mode, is polymer dispersed liquid crystal (PDLC) mode, vertical alignment (VA) mode, and in-plane switching (IPS) mode. The drive systems to which the liquid crystal composition is applicable include static drive, time division drive, active matrix drive, and dual frequency drive.

The perfluoroallyloxy compound of the invention can be combined with a variety of known liquid crystal materials to provide liquid crystal compositions applicable to various electro-optical display devices different in kind of the alignment film or various characteristics such as twist angle, tilt angle, dielectric anisotropy ($\Delta\epsilon$), resistivity, nematic phase range, viscosity, average dielectric constant, coefficient of viscosity, and voltage holding ratio.

With respect to electro-optical display devices and liquid crystal compositions used therein, various proposals have been made, e.g., in JP-A-10-67989, JP-T-3-502942, JP-A-3-85532, JP-A-4-296387, JP-T-6-501517, JP-T-10-512914, JP-A-9-125063, JP-A-11-29771, JP-A-10-245559, JP-A-2000-351972, JP-A-2002-285157, JP-A-2002-302673, JP-T-2002-533526, JP-A-2002-114978, JP-T-5-501735, JP-A-2002-193853, JP-A-2002-193852, JP-T-5-500683, JP-A-2002-201474, JP-A-10-204016, JP-A-2000-73062, JP-A-2000-96056, JP-A-2001-31971, JP-A-2000-80371, JP-A-2001-354967, JP-A-2000-351972, WO 99/21815, WO 99-21816, WO 97/36847, U.S. Pat. Nos. 5,456,860 and 5,578,241, EP 662,502, and German Patent 10117224. The perfluoroallyloxy compound of the present invention can be used in combination with these electro-optical display devices or liquid crystal compositions.

The electro-optical display devices using the perfluoroallyloxy compound of the present invention are useful in applications including watches, calculators, measuring instruments, automotive instrumentation, copiers, cameras, office automation equipment, handheld personal computers, and mobile phones. They are also useful in other applications, such as smart windows, optical shutters, and polarizing beam splitters.

The present invention will now be illustrated in greater detail with reference to Examples, but it should be understood that the invention is not construed as being limited thereto.

EXAMPLE 1

Synthesis of Compound No. 1 ($R_1$: n-$C_3H_7$)

Compound No. 1($R_1$: n-$C_3H_7$) was synthesized as follows according to reaction scheme 1:

Reaction scheme 1:

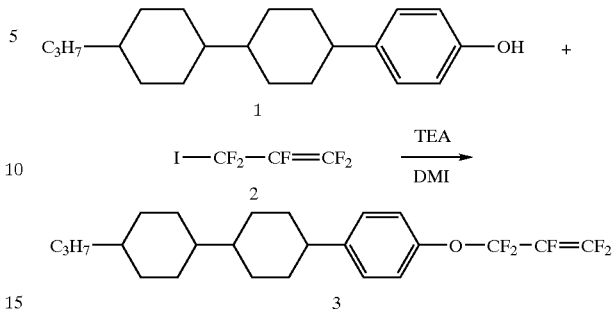

In a nitrogen stream, 1.2 g (4 mmol) of 4-[4-(4-n-propylcyclohexyl)cyclohexyl]phenol (1) was dissolved in 7 g of dimethylimidazolidinone (DMI), and 1.03 g (4 mmol) of 3-iodoperfluoropropene-1 (2) was added to the solution. To the mixture was added 0.48 g (4.8 mmol) of triethylamine (TEA), followed by allowing the mixture to react for 2 hours.

The reaction mixture was subjected to gas chromatography to determine the reaction conversion from the area percentages of the chromatogram. The area percentage of the raw material (1) was 9%, and that of the product (3) was 91%.

The reaction mixture was neutralized by addition of ethyl acetate and hydrochloric acid, washed with water until neutrality was confirmed, dried over magnesium sulfate, and filtered. The filtrate was subjected to solvent exchange with toluene, treated with silica, and concentrated under reduced pressure. The concentrate was purified successively by kugel-rohr distillation and crystallization (first stage: ethyl acetate/methanol=1/18; second stage: acetone) to give 0.8 g (yield; 47%) of the title compound (3) with 99.9% purity as white crystals.

The resulting compound (3) was identified to be compound No. 1 ($R_1$: n-$C_3H_7$) by infrared (IR) absorption spectrum and $^1$H-NMR analyses. The analytical results obtained are shown below.

[IR] 2920 $cm^{-1}$, 2850 $cm^{-1}$, 1794 $cm^{-1}$, 1609 $cm^{-1}$, 1508 $cm^{-1}$, 1447 $cm^{-1}$, 1389 $cm^{-1}$, 1319 $cm^{-1}$, 1223 $cm^{-1}$, and 1196 $cm^{-1}$

[$^1$H-NMR] 7.3–7.0 (m, 4H), 2.6–2.3 (m, 1H), 2.2–0.4 (m, 26H)

EXAMPLE 2

Synthesis of Compound No. 1 ($R_1$: n-$C_3H_7$)

Compound No. 1($R_1$: n-$C_3H_7$) was synthesized as follows according to reaction scheme 2:

Reaction scheme 2:

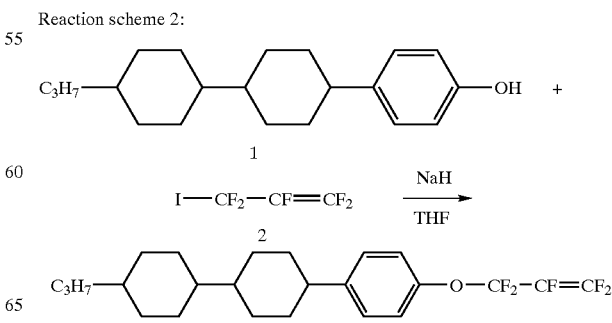

In a nitrogen stream, 2.71 g (5.65 mmol) of sodium hydride and 30 ml of tetrahydrofuran (THF) were put into a reactor, and a solution of 13 g (43.5 mmol) of 4-[4-(4-n-propylcyclohexyl)cyclohexyl]phenol (1) in 120 ml of tetrahydrofuran (THF) was added dropwise. After the mixture was stirred for 30 minutes, 11.2 g (43.5 mmol) of 3-iodoperfluoropropene-1 (2) was dropwise added to the mixture, followed by allowing the mixture to react for 3 hours. The reaction temperature was raised up to 70° C., at which the reaction was further continued for 1 hour.

The reaction mixture was subjected to gas chromatography to determine the reaction conversion from the peak area percentages of the chromatogram. The area percentage of the raw material (1) was 53%, and that of the product (3) was 47%.

The reaction mixture was purified in the same manner as in Example 1 to yield a product (3). IR and $^1$H-NMR analyses on the product (3) gave substantially the same results as in Example 1 whereby the resulting product (3) was identified to be compound No. 1 ($R_1$: n-$C_3H_7$).

EXAMPLE 3

Synthesis of Compound No. 1 ($R_1$: n-$C_3H_7$)
Compound No. 1($R_1$: n-$C_3H_7$) was synthesized as follows according to reaction scheme 3:

Reaction scheme 3:

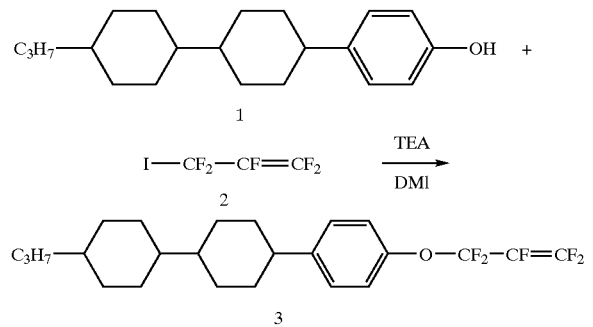

In a nitrogen stream, 13 g (43.5 mmol) of 4-[4-(4-n-propylcyclohexyl)cyclohexyl]phenol (1), 24 g (200 mmol) of triethylamine, and 84 g of dimethylimidazolidinone (DMI) were put into a reactor, followed by heating to 40° C. to prepare a solution. To the solution was dropwise added 9.2 g (40 mmol) of 3-iodoperfluoropropene-1 (2), followed by allowing the mixture to react for 3 hours.

The reaction mixture was subjected to gas chromatography to determine the reaction conversion from the peak area percentages of the chromatogram. The area percentage of the raw material (1) was 0%, and that of the product (3) was 100%.

The reaction mixture was purified in the same manner as in Example 1 to give a product (3). IR and $^1$H-NMR analyses on the product (3) gave substantially the same results as in Example 1 whereby the resulting compound (3) was identified to be compound No. 1 ($R_1$: n-$C_3H_7$).

EXAMPLE 4

Synthesis of Compound No. 1 ($R_1$: n-$C_3H_7$)
Compound No. 1($R_1$: n-$C_3H_7$) was synthesized as follows according to reaction scheme 4:

Reaction scheme 4:

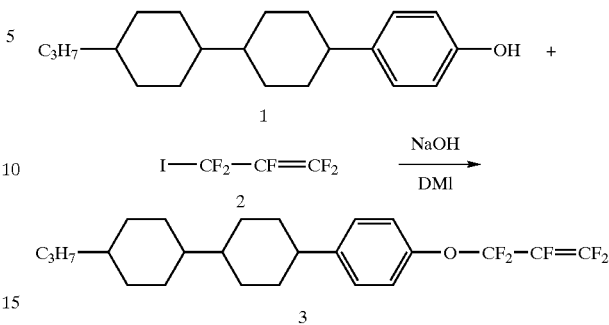

In a nitrogen stream, 12 g (40 mmol) of 4-[4-(4-n-propylcyclohexyl)cyclohexyl]phenol (1) and 19 g (40 mmol) of sodium hydroxide were dissolved in 50 g of dimethylimidazolidinone (DMI). To the solution was added 10.3 g (40 mmol) of 3-iodoperfluoropropene-1 (2), followed by allowing the mixture to react for 3 hours.

The reaction mixture was subjected to gas chromatography to determine the reaction conversion from the peak area percentages of the chromatogram. The area percentage of the raw material (1) was 66%, and that of the product (3) was 34%.

The reaction mixture was purified in the same manner as in Example 1 to give a product (3). IR and $^1$H-NMR analyses on the product (3) gave substantially the same results as in Example 1 whereby the resulting compound (3) was identified to be compound No. 1 ($R_1$: n-$C_3H_7$).

EXAMPLE 5

Synthesis of Compound No. 2 ($R_1$: n-$C_3H_7$)
Compound No. 2 ($R_1$: n-$C_3H_7$) was synthesized as follows according to reaction scheme 5:

Reaction scheme 5:

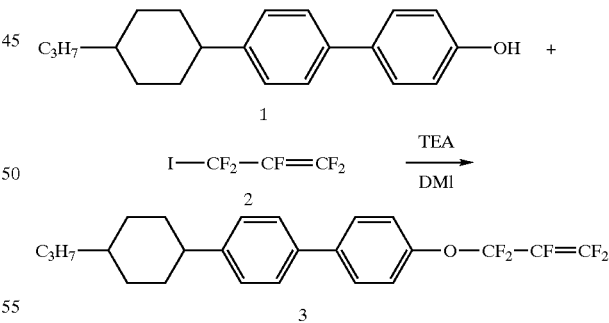

In dimethylimidazolidinone (DMI) was dissolved 2.35 g (8 mmol) of 4-[4-(4-n-propylcyclohexyl)phenyl]phenol (1), and 2.41 g (9.36 mmol, 1.17 eq.) of 35 iodoperfluoropropene-1 (2) was added to the solution. To the mixture was dropwise added 1.37 g (13.5 mmol, 1.7 eq.) of triethylamine over 5 minutes while cooling the mixture with water, followed by allowing the mixture to react for 2 hours.

The reaction mixture was neutralized by addition of ethyl acetate and hydrochloric acid, washed with water, dried over magnesium sulfate, and filtered. The filtrate was concentrated to give a brown solid. The resulting solid was purified successively by column treatment (toluene/hexane=1/1), kugel-rohr distillation, and crystallization (ethyl acetate/methanol=4/6) to give 1.5 g (yield; 44%) of the title compound (3) with 100% purity as white crystals.

The resulting compound (3) was identified to be compound No. 2 ($R_1$: n-$C_3H_7$) by infrared (IR) absorption spectrum analysis and $^1$H-NMR analysis. The analytical results obtained are shown below.

[IR] 2923 $cm^{-1}$, 2851 $cm^{-1}$, 1790 $cm^{-1}$, 1609 $cm^{-1}$, 1497 $cm^{-1}$, 1385 $cm^{-1}$, 1315 $cm^{-1}$, 1219 $cm^{-1}$, 1153 $cm^{-1}$, 1011 $cm^{-1}$, 826 $cm^{-1}$, and 791 $cm^{-1}$

[$^1$H-NMR] 7.7–7.1 (m, 8H), 2.7–2.3 (m, 1H), 2.1–0.8 (m, 16H)

EXAMPLE 6

Synthesis of Compound No. 3 ($R_1$: n-$C_3H_7$)

Compound No. 3 ($R_1$: n-$C_3H_7$) was synthesized as follows according to reaction scheme 6:

Reaction scheme 6:

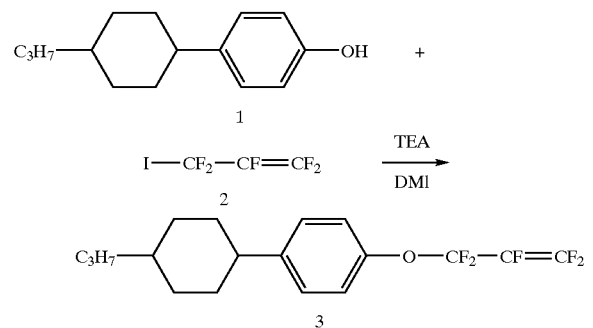

In a flask purged with argon were put 2.0 g (9.2 mmol) of 4-(4-n-propylcyclohexyl)phenol (1), 2.37 g (9.2 mmol, 1.0 eq.) of 3-iodoperfluoropropene-1 (2), and 10 g of dimethylimidazolidinone (DMI). While the resulting mixture was stirred under ice cooling, 1.2 g (1.2 mmol, 1.3 eq.) of triethylamine (TEA) was added thereto dropwise. After the addition, the mixture was further allowed to react for an addition 10 minute period while cooling with ice. The reaction mixture was treated with water, extracted with hexane, washed with water until neutrality, dried over magnesium sulfate, and evaporated to remove the solvent. The residue was purified successively by column treatment (hexane), distillation, and crystallization (methanol) to afford 0.7 g (yield; 24.1%) of the title compound (3) with 99.8% purity as a colorless liquid.

The resulting product (3) was identified to be compound No. 3 ($R_1$: n-$C_3H_7$) by infrared absorption spectrum analysis (IR) and $^1$H-NMR analysis. The analytical results obtained are shown below.

[IR] 2859 $cm^{-1}$, 2924 $cm^{-1}$, 1851 $cm^{-1}$, 1790 $cm^{-1}$, 1670 $cm^{-1}$, 1593 $cm^{-1}$, 1508 $cm^{-1}$, 1450 $cm^{-1}$, 1385 $cm^{-1}$, 1315 $cm^{-1}$, 1219 $cm^{-1}$, 1157 $cm^{-1}$, and 1018 $cm^{-1}$

[$^1$H-NMR] 7.3–7.1 (m, 4H), 1.9–0.9 (m, 17H)

EXAMPLE 7

Each of compound Nos. 1 to 3 obtained in Examples 1, 5, and 6 was added to mother liquid crystal 1 or 2, whose formulation is shown below, in an amount of 10% by mass to prepare a liquid crystal composition.

The resulting liquid crystal compositions were measured for NI point, optical anisotropy (Δn), viscosity (η), and dielectric anisotropy (Δε). Furthermore, extrapolated values of these characteristics were obtained. The results of measurement are shown in Table 1, and the extrapolated values in Table 2. In Tables, NI↑ stands for the NI point in temperature rise, and NI↓ in temperature drop.

TABLE 1

| Mother Liquid Crystal | Compound No. | NI↑ | NI↓ | Δn | η | Δε |
|---|---|---|---|---|---|---|
| 1 | — | 52 | 52 | 0.119 | 23 | 10.8 |
| 2 | No. 1 (Example 1) | 58 | 57 | 0.112 | 22 | 10.2 |
| 1 | — | 84.3 | 83.4 | 0.0866 | 23.3 | 4.95 |
| 1 | No. 1 (Example 1) | 91.8 | 91.0 | 0.0872 | 21.4 | 4.88 |
| 1 | No. 2 (Example 5) | 90.1 | 89.6 | 0.0939 | 22.2 | 4.96 |
| 1 | No. 3 (Example 6) | 73.9 | 73.0 | 0.0837 | 18.5 | 4.72 |

TABLE 2

| Mother Liquid Crystal | Compound No. | NI↑ | NI↓ | Δn | η | Δε |
|---|---|---|---|---|---|---|
| 1 | No. 1 (Example 1) | 159 | 159 | 0.0926 | 4.14 | 4.3 |
| 2 | No. 1 (Example 1) | 110 | 102 | 0.049 | 12.6 | 4.8 |
| 1 | No. 2 (Example 5) | 142 | 145 | 0.1596 | 12.5 | 5.0 |
| 1 | No. 3 (Example 6) | -19.7 | -20.7 | 0.0576 | -25.5 | 2.7 |

It is seen from the results in Tables 1 and 2 that the tricyclic ones of the perfluoroallyloxy compounds of the present invention have a low viscosity and a high NI point and that the bicyclic ones are expected to reduce the viscosity of a mother liquid crystal to which they are added.

EXAMPLE 8

Synthesis of Compound No. 4 ($R_1$: $C_2H_5$)

Compound No. 4 ($R_1$: $C_2H_5$) was synthesized as follows according to reaction scheme 7:

Reaction scheme 7:

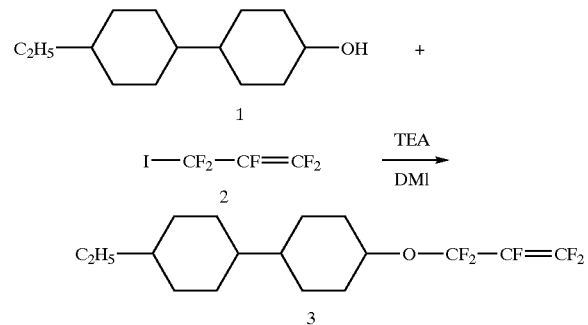

In a flask purged with argon were put 0.57 g (2.71 mmol) of 4-(4-ethylcyclohexyl)cyclohexanol (1) and 1.65 g (16.3 mmol, 6.0 eq.) of triethylamine (TEA), followed by heating under reflux for 1 hour. The mixture was cooled to −20° C., and a solution of 0.70 g (11.6 mmol, 4.3 eq.) of 3-iodoperfluoropropene-1 (2) in 1 ml of dimethylimidazolidinone (DMI) was added thereto dropwise over 1 hour, followed by stirring at room temperature for 14 hours. A 4% hydrochloric acid aqueous solution and toluene were added to the reaction mixture for liquid—liquid separation. The organic layer was washed successively with water, a sodium hydrogencarbonate aqueous solution, and water until neutrality and dried over magnesium sulfate. The solvent was removed by evaporation. The residue was purified by silica gel column chromatography (hexane) to give 0.26 g (yield; 27.3%) of the title compound (3) with 99.9% purity as a colorless liquid.

The resulting product (3) was identified to be compound No. 4 ($R_1$: $C_2H_5$) by infrared absorption spectrum analysis (IR) and $^1$H-NMR analysis. The analytical results obtained are shown below.

[IR] 2924 $cm^{-1}$, 2855 $cm^{-1}$, 2360 $cm^{-1}$, 2341 $cm^{-1}$, 1790 $cm^{-1}$, 1450 $cm^{-1}$, 1381 $cm^{-1}$, 1315 $cm^{-1}$, 1223 $cm^{-1}$, 1173 $cm^{-1}$, 1026 $cm^{-1}$, 991 $cm^{-1}$, 960 $cm^{-1}$, 934 $cm^{-1}$, 899 $cm^{-1}$, 795 $cm^{-1}$, and 664 $cm^{-1}$

[$^1$H-NMR] 4.5–4.0 (m, 1H), 2.2–0.4 (m, 24H)

EXAMPLE 9

Synthesis of Compound No. 19 ($R_1$: n-$C_5H_{11}$)

Compound No. 19 ($R_1$: n-$C_5H_{11}$) was synthesized as follows according to reaction scheme 8:

Reaction scheme 8:

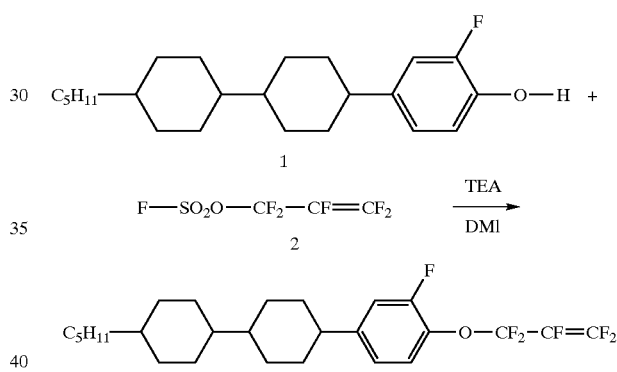

In a thoroughly dried flask were put 2 g (5.77 mmol) of 4-[4-(4-n-pentylcyclohexyl)]cyclohexyl-2-fluorophenol (1), 14 g of dimethylimidazolidinone (DMI), and 4 g (3.95 mmol) of triethylamine (TEA), followed by stirring under ice cooling. After the mixture was cooled to 3° C., 2.4 g (1.8 eq.) of perfluoroallyl fluorosulfite (2) was slowly added dropwise. After 15 minutes from completion of the dropwise addition, ethyl acetate and water were added to the reaction mixture for oil/water phase separation. The oily phase was dried over magnesium sulfate and freed of the solvent. Hexane was added to the residue, followed by filtration to remove any insoluble matter. The filtrate was purified successively by column chromatography and crystallization from ethanol to give 0.6 g (yield; 21.5%) of the title compound (3) with 99.9% purity as a colorless solid.

The resulting product (3) was identified to be compound No. 19 ($R_1$: n-$C_5H_{11}$) by infrared absorption spectrum analysis (IR) and $^1$H-NMR analysis. The analytical results obtained are shown below.

[IR] 2920 $cm^{-1}$, 2851 $cm^{-1}$, 1790 $cm^{-1}$, 1597 $cm^{-1}$, 1512 $cm^{-1}$, 1447 $cm^{-1}$, 1385 $cm^{-1}$, 1319 $cm^{-1}$, 1265 $cm^{-1}$, 1211 $cm^{-1}$, 1150 $cm^{-1}$, 1115 $cm^{-1}$, 1018 $cm^{-1}$, 953 $cm^{-1}$, 864 $cm^{-1}$, and 795 $cm^{-1}$

[$^1$H-NMR] 7.2–6.8 (m, 3H), 2.6–2.2 (m, 1H), 2.1–0.7 (m, 1H)

EXAMPLE 10

Synthesis of Compound No. 18 ($R_1$: n-$C_5H_{11}$)

Compound No. 18 ($R_1$: n-$C_5H_{11}$) was synthesized as follows according to reaction scheme 9:

Reaction scheme 9:

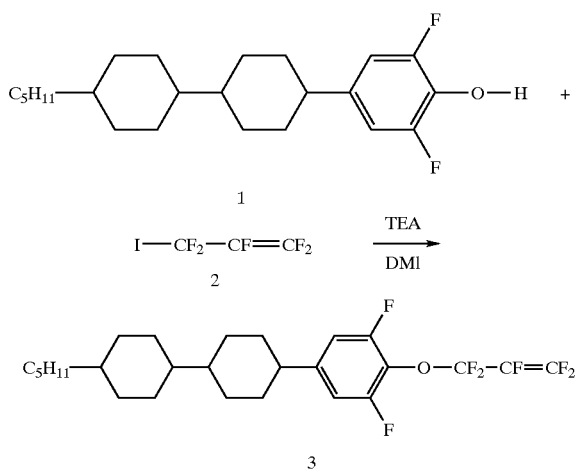

In a flask were put 5 g (13.7 mmol, 1.00 eq.) of 4-[4-(4-n-pentylcyclohexyl)cyclohexyl]-1,6-fluorophenol (1), 2.08 g (20.6 mmol, 1.50 eq.) of triethylamine (TEA), and 25 g of dimethylimidazolidinone (DMI) and dissolved, followed by cooling with ice. To the mixture under stirring and ice-cooling was dropwise added 3.54 g (13.7 mmol, 1.00 eq.) of 3-iodoperfluoropropene-1 (2). After the addition, the reaction was continued for an addition 10 minute period while cooling with ice. Hydrochloric acid was added thereto dropwise, and the reaction mixture was phase separated into an aqueous phase and an oily phase. The oily phase was washed with water, dried over magnesium sulfate, and freed of the solvent. The residue was purified successively by silica gel column chromatography (hexane), kugel-rohr distillation (158–215° C., 017–1.0 mmHg), and crystallization from ethyl acetate/methanol (1/1) to give 2.07 g (yield; 30.5%) of the title compound (3) with 99.8% purity as a colorless solid.

The resulting product (3) was identified to be compound No. 18 ($R_1$: n-$C_5H_{11}$) by infrared absorption spectrum analysis (IR) and $^1$H-NMR analysis. The analytical results obtained are shown below.

[IR] 2924 cm$^{-1}$, 2853 cm$^{-1}$, 1790 cm$^{-1}$, 1630 cm$^{-1}$, 1601 cm$^{-1}$, 1514 cm$^{-1}$, 1447 cm$^{-1}$, 1385 cm$^{-1}$, 1346 cm$^{-1}$, 1319 cm$^{-1}$, 1202 cm$^{-1}$, 1148 cm$^{-1}$, 1113 cm$^{-1}$, 1018 cm$^{-1}$, 959 cm$^{-1}$, 943 cm$^{-1}$, 895 cm$^{-1}$, 851 cm$^{-1}$, 824 cm$^{-1}$, 725 cm$^{-1}$, 708 cm$^{-1}$, 665 cm$^{-1}$, 646 cm$^{-1}$, 619 cm$^{-1}$, and 527 cm$^{-1}$

[$^1$H-NMR] 6.9–6.7 (d, 2H), 2.6–0.5 (m, 31H)

EXAMPLE 11

Synthesis of Compound No. 14 ($R_1$: n-$C_5H_{11}$)

Compound No. 14 ($R_1$: n-$C_5H_{11}$) was synthesized as follows according to reaction scheme 10:

Reaction scheme 10:

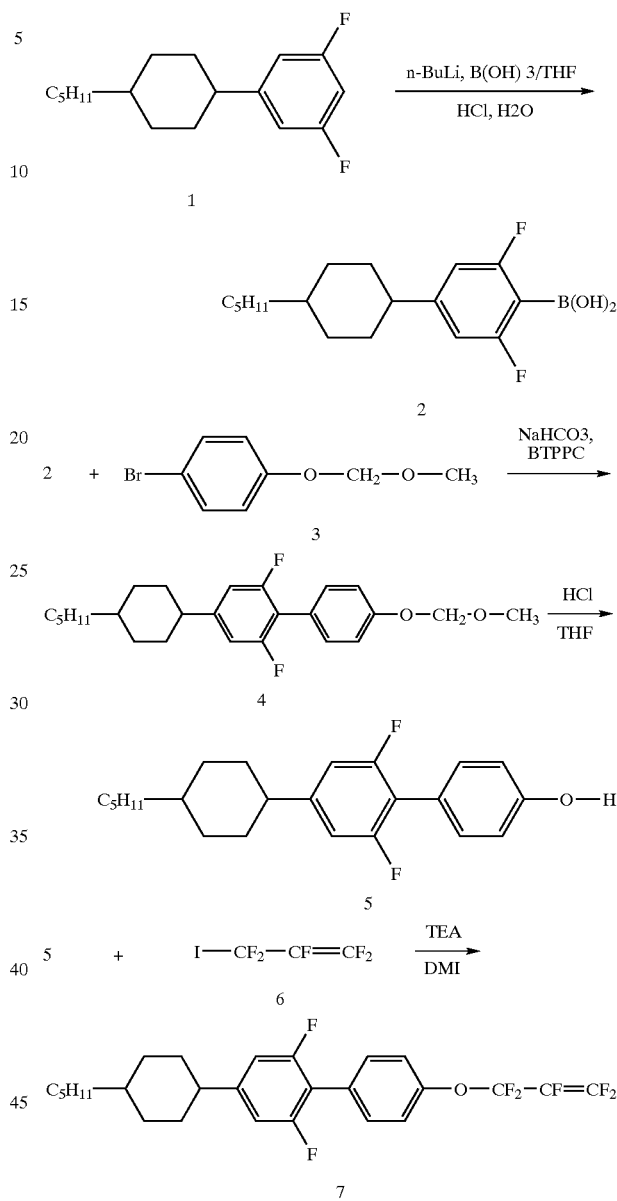

In a flask purged with argon were put 7.98 g (0.03 mol) of 5-(4-n-pentylcyclohexyl)-1,3-difluorobenzene (1) and 65 ml of tetrahydrofuran (THF). The mixture was cooled with a methanol/dry ice coolant to −50° C. or lower, and 13.5 ml (0.0351 mol) of a 2.6 mol/l hexane solution of n-butyl lithium was added thereto, followed by stirring for 1 hour. To the reaction mixture kept at −50° C. or lower was then added dropwise 3.57 g (0.0343 mol, 1.14 eq.) of dimethoxy-boron, followed by stirring for 1 hour. After returning to room temperature, 11 ml of a hydrochloric acid aqueous solution (1.2 mol/l) was added thereto dropwise, followed by oil/water phase separation. The oily phase was washed three times with brine, dried over magnesium sulfate, and freed of the solvent to give 6.62 g of 4-(4-n-pentylcyclohexyl)-2,6-difluorophenylboronic acid (2).

In a flask were charged 4.56 g (0.021 mol) of 4-methoxymethoxy-1-bromobenzene (3), 5.3 g (0.021 mol) of sodium hydrogencarbonate, 0.147 g (0.021 mol) of Pd[PPh$_3$]

$_2Cl_2$ complex, 20 ml of toluene, and 40 ml of water in an argon stream. The mixture was heated to 75 to 78° C., and a solution of 6.51 g (0.021 mol) of the boronic acid (2) in 20 ml of ethanol was added dropwise thereto, followed by allowing the mixture to react for 1 hour. After cooling, the reaction mixture was separated into an aqueous phase and an oily phase. After confirming the neutrality of the oily phase, the oily phase was dried over magnesium sulfate and freed of the solvent to afford 8.64 g of 4-[4-(4-n-pentylcyclohexyl)-2,6-fluorophenyl]-1-methoxymethoxybenzene (4).

In a flask were put 8.45 g of the methoxymethoxy compound (4), 4.38 g of hydrochloric acid, and 35 ml of tetrahydrofuran (THF), and the mixture was allowed to react at 70° C. for 2 hours while stirring. Toluene and water were added to the reaction mixture, followed by liquid—liquid separation. After confirming neutrality, the organic phase was dried over magnesium sulfate, freed of the solvent, and crystallized from ethyl acetate to give 4.9 g of 4-[4-(4-n-pentylcyclohexyl)-2,6-fluorophenyl]phenol (5).

In a flask, 2.87 g (8 mmol) of the phenol compound (5) was dissolved in 15 g of dimethylimidazolidinone (DMI). To the solution was added 2.06 g (8 mmol) of 3-iodoperfluoropropene-1 (6), and 1.21 g (8 mmol) of triethylamine (TEA) was added thereto dropwise at 29 to 33° C. The mixture was allowed to react at 25 to 30° C. for 2 hours. After cooling, the reaction mixture was phase separated by addition of ethyl acetate and water. The oily phase was washed with water until neutrality, dried over magnesium sulfate, and freed of the solvent. The residue was purified by column chromatography (hexane), kugel-rohr distillation (215° C., 0.35 mmHg), and crystallized from ethyl acetate/methanol (1/3) to give 0.44 g (yield; 10.2%) of the title compound (7) with 99.8% purity as a colorless solid.

The resulting product (7) was identified to be compound No. 14 ($R_1$: n-$C_5H_{11}$) by infrared absorption spectrum analysis (IR) and $^1$H-NMR analysis. The analytical results obtained are shown below.

[IR] 2928 $cm^{-1}$, 2851 $cm^{-1}$, 1794 $cm^{-1}$, 1639 $cm^{-1}$, 1566 $cm^{-1}$, 1485 $cm^{-1}$, 1431 $cm^{-1}$, 1385 $cm^{-1}$, 1315 $cm^{-1}$, 1218 $cm^{-1}$, 1188 $cm^{-1}$, 1161 $cm^{-1}$, 1057 $cm^{-1}$, 1011 $cm^{-1}$, 949 $cm^{-1}$, 845 $cm^{-1}$, 791 $cm^{-1}$, 725 $cm^{-1}$, 656 $cm^{-1}$, 613 $cm^{-1}$, and 529 $cm^{-1}$

[$^1$H-NMR] 7.7–7.1 (m, 4H), 7.0–6.7 (m, 2H), 2.7–2.3 (m, 1H), 2.2–0.8 (m, 20H)

EXAMPLE 12

Synthesis of Compound No. 11 ($R_1$: n-$C_3H_7$)

Compound No. 11 ($R_1$: n-$C_3H_7$) was synthesized as follows according to reaction scheme 11:

Reaction scheme 11:

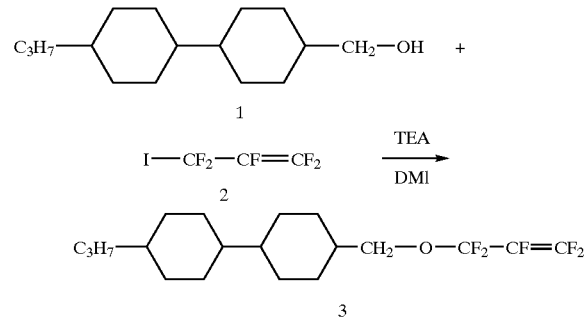

In a flask purged with argon were charged 6.2 g (26.1 mmol) of 4-(4-propylcyclohexyl)cyclohexylmethanol (1) and 15.8 g (156 mmol, 6.0 eq.) of triethylamine (TEA), followed by heating under reflux for 1 hour. After cooling to −20° C., 7.9 g (30.8 mmol, 1.18 eq.) of 3-iodoperfluoropropene-1 (2) was slowly added thereto dropwise, followed by stirring at room temperature. The reaction mixture was phase separated by addition of a hydrochloric acid aqueous solution (9.6 g hydrochloric acid in 24 g water) and 30 ml of toluene. The organic phase was washed with water, dried over magnesium sulfate, and freed of the solvent. The residue was subjected to column chromatography (hexane) to furnish 2.1 g (yield; 21.6%) of the title compound (3) with 99.8% purity as a colorless transparent liquid.

The resulting product (3) was identified to be compound No. 11 ($R_1$: n-$C_3H_7$) by infrared absorption spectrum analysis (IR) and $^1$H-NMR analysis. The analytical results obtained are shown below.

[IR] 2920 $cm^{-1}$, 2851 $cm^{-1}$, 2623 $cm^{-1}$, 1790 $cm^{-1}$, 1450 $cm^{-1}$, 1412 $cm^{-1}$, 1377 $cm^{-1}$, 1315 $cm^{-1}$, 1211 $cm^{-1}$, 1173 $cm^{-1}$, 1033 $cm^{-1}$, 964 $cm^{-1}$, 941 $cm^{-1}$, 899 $cm^{-1}$, 806 $cm^{-1}$, 783 $cm^{-1}$, 741 $cm^{-1}$, 664 $cm^{-1}$, 613 $cm^{-1}$, and 513 $cm^{-1}$

[$^1$H-NMR] 3.9–3.7 (d, 2H), 2.2–0.5 (m, 27H)

EXAMPLE 13

In Table 3 below are shown the phase transition temperatures (° C.), optical anisotropy ($\Delta n$), and dielectric anisotropy ($\Delta \epsilon$) of the perfluoroallyloxy compounds according to the present invention. The optical anisotropy ($\Delta n$) and the dielectric anisotropy ($\Delta \epsilon$) are extrapolated values obtained from the results of measurement on liquid crystal compositions prepared by adding 10% by mass of the test compound to the above-described mother liquid crystal 1.

In Table 3, compound Nos. 1 ($R_1$: n-$C_5H_{11}$), 5, 8, 9, and 10 are those prepared in accordance with Example 1; compound Nos. 17, 19 ($R_1$: n-$C_3H_7$) and 21 are those prepared in accordance with Example 9; and compound Nos. 15, 16, 18 ($R_1$: n-$C_3H_7$), and 20 are those prepared in accordance with Example 10.

TABLE 3

| Compound No. | $R_1$ | Phase Transition Temperatures (° C.) | $\Delta n$ | $\Delta \epsilon$ |
|---|---|---|---|---|
| 1 (Example 1) | n-$C_3H_7$ | Sm→157.3→N→174.2→I | 0.0926 | 4.3 |
| 1 | n-$C_5H_{11}$ | Sm→171.7→N→178.7→I |  | 4.3 |
| 2 (Example 5) | n-$C_3H_7$ | C→45.5→Sm→169.6→N→180.4→I | 0.1596 | 5.0 |
| 3 (Example 6) | n-$C_3H_7$ | liquid | 0.0576 | 2.7 |
| 4 (Example 8) | $C_2H_5$ | liquid | 0.0331 | 2.97 |
| 5 | n-$C_3H_7$ | C→77→I |  |  |
| 8 | n-$C_4H_9$ | C→59.6→I |  |  |
| 9 | n-$C_6H_{13}$ | C→33→Sm→53.4→I |  |  |
| 10 | n-$C_8H_{17}$ | Sm→195→I |  |  |
| 11 (Example 12) | n-$C_3H_7$ | liquid | 0.0141 | 0.238 |
| 14 (Example 11) | n-$C_5H_{11}$ | C→67.1→Sm→84.9→N→114.1→I | 0.126 | 8.47 |
| 15 | n-$C_3H_7$ | C→31.8→N→132.4→I | 0.1458 | 8.00 |
| 16 | n-$C_5H_{11}$ | liquid | 0.0536 | 5.24 |
| 17 | n-$C_5H_{11}$ | liquid | 0.061 | 4.55 |
| 18 | n-$C_3H_7$ | Sm→41.2→N→166.6→I | 0.1006 | 7.3 |

TABLE 3-continued

| Compound No. | $R_1$ | Phase Transition Temperatures (° C.) | $\Delta n$ | $\Delta\epsilon$ |
|---|---|---|---|---|
| 18 (Example 10) | n-$C_5H_{11}$ | N→165.2→I | 0.0916 | 7.35 |
| 19 | n-$C_3H_7$ | Sm→49.8→N→170.8→I | 0.1036 | 5.0 |
| 19 (Example 9) | n-$C_5H_{11}$ | Sm→44.4→N→170.3→I | 0.101 | 6.0 |
| 20 | n-$C_3H_7$ | N→146.2→I | | |
| 21 | n-$C_5H_{11}$ | Sm→101.5→N→168.3→I | | |

C: solid phase, Sm: smectic phase, N: nematic phase, I: isotropic phase

The results in Table 3 prove usefulness of the perfluoroallyloxy compounds of the present invention as a liquid crystal material.

EXAMPLE 14

Liquid crystal compositions were prepared using the perfluoroallyloxy compounds of the present invention according to the formulations shown in Table 4 below. The NI point, optical anisotropy ($\Delta n$), dielectric anisotropy ($\Delta\epsilon$), and viscosity ($\eta$) of the compositions were measured. The results of measurement are also shown in Table 4.

TABLE 4

| | Liquid Crystal Composition*1 | | | |
|---|---|---|---|---|
| Liquid Crystal Compound | 1 | 2 | 3 | 4 |
| C2-CY-CY-PH-3,4-diF | 16 | 13 | | 11 |
| C3-CY-CY-PH-3,4-diF | 17 | 14 | | 12 |
| C5-CY-CY-PH-3,4-diF | 16 | 13 | | 12 |
| C3-CY-PH-3,4-diF | 14 | 5 | | |
| C5-CY-PH-3,4-diF | 14 | 5 | | |
| C2-CY-C≡C-PH-3,4-diF | 2 | | | |
| C5-CY-PH-Cl | 7 | | | |
| C3-CY-PH-$OCH_3$ | 5 | | | |
| C7-CY-PH-F | 4 | | | |
| C5-CY-PH-F | | 5 | | |
| C3-CY-PH-$OCF_2CF=CF_2$ (compound No. 3) | | 14 | 10 | 5 |
| C3-CY-PH3F—$OCF_2CF=CF_2$ (compound No. 17) | | | 15 | |
| C5-CY-PH3F—$OCF_2CF=CF_2$ (compound No. 17) | | 13 | 15 | 25 |
| C3-CY-CY-PH3F—$OCF_2CF=CF_2$ (compound No. 19) | | | 16 | |
| C5-CY-CY-PH3F—$OCF_2CF=CF_2$ (compound No. 19) | | | 16 | |
| C3-CY-CY-PH3,5-diF—$OCF_2CF=CF_2$ (compound No. 18) | | | 14 | 11 |
| C5-CY-CY-PH3,5-diF—$OCF_2CF=CF_2$ (compound No. 18) | 3 | 18 | 14 | 12 |
| C3-CY-PH-PH3,5-diF—$OCF_2CF=CF_2$ (compound No. 15) | | 2 | | 12 |
| Results of Measurement | NI Point (° C.) | 83.0 | 94.7 | 88.8 | 85.2 |
| | $\Delta n$ (25° C.) | 0.0991 | 0.0870 | 0.0852 | 0.0872 |
| | $\Delta\epsilon$ (25° C.) | 5.1 | 4.9 | 4.9 | 5.4 |
| | $\eta$ (mPa · s) | 20 | 17 | 14 | 17 |

CY: 1,4-cyclohexylene, PH: 1,4-phenylene, Cn: straight-chain alkyl group having n carbon atoms and, unless otherwise indicated, bonded to the 4-position
*1: in terms of parts by mass It is seen from Table 4 that use of the perfluoroallyloxy compounds of the present invention provides liquid crystal compositions having a low viscosity, a small refractive index anisotropy ($\Delta n$), a large dielectric anisotropy ($\Delta\epsilon$), and a high NI point (broad nematic phase range).

EXAMPLE 15

Synthesis of Compound No. 22 ($R_1$: n-$C_3H_7$) and Phase Transition Temperatures Compound no. 22 ($R_1$: n-$C_3H_7$) shown below was synthesized in accordance with Example 9. As a result of infrared absorption spectrum analysis (IR) and $^1$H-NMR analysis, the resulting product was identified to be compound No. 22 ($R_1$: n-$C_3H_7$). The results of analyses are shown below.

Compound No. 22

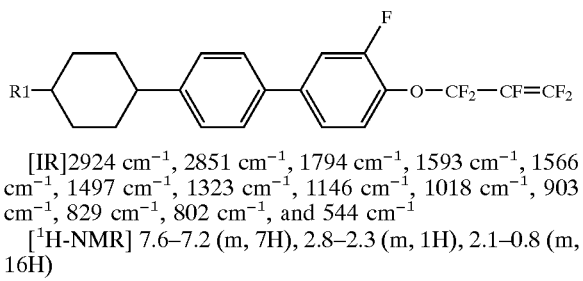

[IR] 2924 $cm^{-1}$, 2851 $cm^{-1}$, 1794 $cm^{-1}$, 1593 $cm^{-1}$, 1566 $cm^{-1}$, 1497 $cm^{-1}$, 1323 $cm^{-1}$, 1146 $cm^{-1}$, 1018 $cm^{-1}$, 903 $cm^{-1}$, 829 $cm^{-1}$, 802 $cm^{-1}$, and 544 $cm^{-1}$

[$^1$H-NMR] 7.6–7.2 (m, 7H), 2.8–2.3 (m, 1H), 2.1–0.8 (m, 16H)

The phase transition temperatures (° C.) of the resulting compound No. 22 ($R_1$: n-$C_3H_7$) were as follows.

C→46→Sm→129→N→152→I

EXAMPLE 16

Synthesis of Compound No. 23 ($R_1$: n-$C_5H_{11}$)

Compound No. 23 ($R_1$: n-$C_5H_{11}$) shown below was synthesized in accordance with Example 9. As a result of infrared absorption spectrum analysis (IR) and $^1$HNMR analysis, the resulting product was identified to be compound No. 23 ($R_1$: n-$C_5H_{11}$). The results of analyses are shown below.

Compound No. 23

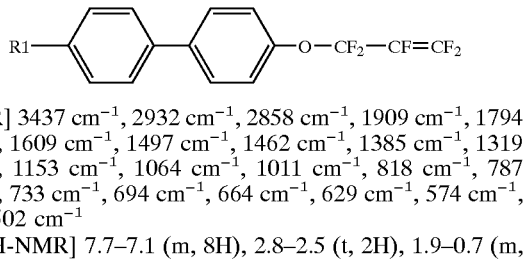

[IR] 3437 $cm^{-1}$, 2932 $cm^{-1}$, 2858 $cm^{-1}$, 1909 $cm^{-1}$, 1794 $cm^{-1}$, 1609 $cm^{-1}$, 1497 $cm^{-1}$, 1462 $cm^{-1}$, 1385 $cm^{-1}$, 1319 $cm^{-1}$, 1153 $cm^{-1}$, 1064 $cm^{-1}$, 1011 $cm^{-1}$, 818 $cm^{-1}$, 787 $cm^{-1}$, 733 $cm^{-1}$, 694 $cm^{-1}$, 664 $cm^{-1}$, 629 $cm^{-1}$, 574 $cm^{-1}$, and 502 $cm^{-1}$

[$^1$H-NMR] 7.7–7.1 (m, 8H), 2.8–2.5 (t, 2H), 1.9–0.7 (m, 9H)

EXAMPLE 17

Synthesis of Compound No. 24 ($R_1$: n-$C_3H_7$)

Compound No. 24 ($R_1$: n-$C_3H_7$) shown below was synthesized in accordance with Example 9. As a result of infrared absorption spectrum analysis (IR) and $^1$HNMR analysis, the resulting product was identified to be compound No. 24 ($R_1$: n-$C_3H_7$). The results of analyses are shown below.

Compound No. 24

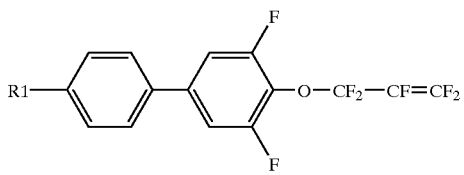

[IR] 2963 cm$^{-1}$, 2936 cm$^{-1}$, 2874 cm$^{-1}$, 1790 cm$^{-1}$, 1628 cm$^{-1}$, 1601 cm$^{-1}$, 1567 cm$^{-1}$, 1528 cm$^{-1}$, 1501 cm$^{-1}$, 1443 cm$^{-1}$, 1385 cm$^{-1}$, 1319 cm$^{-1}$, 1277 cm$^{-1}$, 1234 cm$^{-1}$, 1207 cm$^{-1}$, 1146 cm$^{-1}$, 1111 cm$^{-1}$, 1042 cm$^{-1}$, 1018 cm$^{-1}$, 895 cm$^{-1}$, 864 cm$^{-1}$, 837 cm$^{-1}$, 667 cm$^{-1}$, and 536 cm$^{-1}$

[$^1$H-NMR] 7.5–7.1 (m, 6H), 2.7–2.5 (t, 2H), 1.9–1.5 (m, 2H), 1.1–0.9 (t, 3H)

EXAMPLE 18

Synthesis of Compound No. 25 ($R_1$: n-$C_3H_7$)

Compound No. 25 ($R_1$: n-$C_3H_7$) shown below was synthesized in accordance with Example 9. As a result of infrared absorption spectrum analysis (IR) and $^1$HNMR analysis, the resulting product was identified to be compound No. 25 ($R_1$: n-$C_3H_7$). The results of analyses are shown below.

Compound No. 25

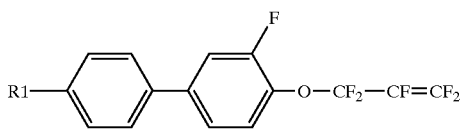

[IR] 2963 cm$^{-1}$, 2936 cm$^{-1}$, 2874 cm$^{-1}$, 1790 cm$^{-1}$, 1593 cm$^{-1}$, 1566 cm$^{-1}$, 1497 cm$^{-1}$, 1466 cm$^{-1}$, 1431 cm$^{-1}$, 1385 cm$^{-1}$, 1319 cm$^{-1}$, 1265 cm$^{-1}$, 1200 cm$^{-1}$, 1150 cm$^{-1}$, 1119 cm$^{-1}$, 1018 cm$^{-1}$, 903 cm$^{-1}$, 876 cm$^{-1}$, 833 cm$^{-1}$, 795 cm$^{-1}$, 667 cm$^{-1}$, and 532 cm$^{-1}$

[$^1$H-NMR] 7.6–7.1 (m, 7H), 2.7–2.5 (t, 2H), 1.9–1.5 (m, 2H), 1.1–0.9 (t, 3H)

EXAMPLE 19

Synthesis of Compound No. 26 ($R_1$: n-$C_3H_7$)

Compound No. 26 ($R_1$: n-$C_3H_7$) shown below was synthesized in accordance with Example. 9. As a result of infrared absorption spectrum analysis (IR) and $^1$HNMR analysis, the resulting product was identified to be compound No. 26 ($R_1$: n-$C_3H_7$). The results of analyses are shown below.

Compound No. 26

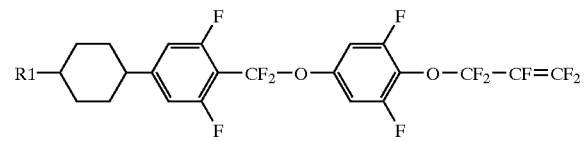

[IR] 3445 cm$^{-1}$, 2936 cm$^{-1}$, 2858 cm$^{-1}$, 1794 cm$^{-1}$, 1639 cm$^{-1}$, 1585 cm$^{-1}$, 1504 cm$^{-1}$, 1454 cm$^{-1}$, 1389 cm$^{-1}$, 1327 cm$^{-1}$, 1300 cm$^{-1}$, 1215 cm$^{-1}$, 1196 cm$^{-1}$, 1150 cm$^{-1}$, 1107 cm$^{-1}$, 1050 cm$^{-1}$, 1018 cm$^{-1}$, 949 cm$^{-1}$, 856 cm$^{-1}$, 822 cm$^{-1}$, 799 cm$^{-1}$, 710 cm$^{-1}$, 663 cm$^{-1}$, 629 cm$^{-1}$, 606 cm$^{-1}$, 571 cm$^{-1}$, 544 cm$^{-1}$, and 525 cm$^{-1}$

[$^1$H-NMR] 7.2–6.4 (m, 4H), 2.7–0.5 (m, 17H)

EXAMPLE 20

Synthesis of Compound No. 27 ($R_1$: n-$C_3H_7$)

Compound No. 27 ($R_1$: n-$C_3H_7$) shown below was synthesized in accordance with Example 9. As a result of infrared absorption spectrum analysis (IR) and $^1$HNMR analysis, the resulting product was identified to be compound No. 27 ($R_1$: n-$C_3H_7$). The results of analyses are shown below.

Compound No. 27

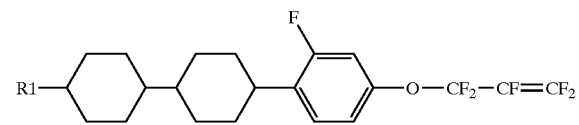

[IR] 3437 cm$^{-1}$, 2924 cm$^{-1}$, 2851 cm$^{-1}$, 1794 cm$^{-1}$, 1593 cm$^{-1}$, 1504 cm$^{-1}$, 1389 cm$^{-1}$, 1319 cm$^{-1}$, 1261 cm$^{-1}$, 1207 cm$^{-1}$, 1150 cm$^{-1}$, 1099 cm$^{-1}$, 1022 cm$^{-1}$, 957 cm$^{-1}$, 872 cm$^{-1}$, 795 cm$^{-1}$, and 621 cm$^{-1}$

[$^1$H-NMR] 7.3–6.7 (m, 4H), 2.9–2.5 (m, 1H), 2.1–0.5 (m, 21H)

EXAMPLE 21

Synthesis of Compound No. 28

Compound No. 28 shown below was synthesized in accordance with Example 9. As a result of infrared absorption spectrum analysis (IR) and $^1$H-NMR analysis, the resulting product was identified to be compound No. 28. The results of analyses are shown below.

Compound No. 28

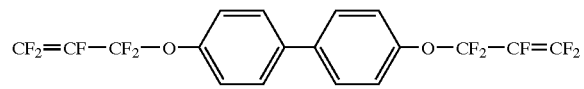

[IR] 3433 cm$^{-1}$, 1794 cm$^{-1}$, 1497 cm$^{-1}$, 1389 cm$^{-1}$, 1319 cm$^{-1}$, 1227 cm$^{-1}$, 1150 cm$^{-1}$, 1069 cm$^{-1}$, 1015 cm$^{-1}$, and 787 cm$^{-1}$

[$^1$H-NMR] 7.7–7.1 (m, 8H)

EXAMPLE 22

In Table 5 below are shown the phase transition temperatures (° C.), optical anisotropy (Δn), and dielectric anisotropy (Δε) of the perfluoroallyloxy compounds according to the present invention. The optical anisotropy (Δn) and the dielectric anisotropy (Δε) are extrapolated values obtained from the results of measurement on liquid crystal compositions prepared by adding 10% by mass of the test compound to the above-described mother liquid crystal 1.

In Table 5, compound Nos. 15, 18, and 19 are those prepared in accordance with Example 9.

TABLE 5

| Compound No. | R₁ | Phase Transition Temp. (° C.) | $\Delta n$ | $\Delta \epsilon$ |
|---|---|---|---|---|
| 15 | C₂H₅ | C→53.8→N→104.6→I | 0.1374 | 7.1 |
| 15 | n-C₄H₉ | C→32.4→N→127.1→I | 0.0924 | 6.17 |
| 15 | n-C₅H₁₁ | Sm→27.9→N→132.6→I | 0.1508 | 8.27 |
| 18 | n-C₄H₉ | C→33.6→N→165.8→I | 0.924 | 6.17 |
| 19 | C₂H₅ | Sm→45.0→N→140.8→I | 0.094 | 4.5 |
| 23 (Example 16) | n-C₅H₁₁ | C→98.2→I | 0.1174 | 2.15 |
| 24 (Example 17) | n-C₃H₇ | liquid | 0.1024 | 6.3 |
| 25 (Example 18) | n-C₃H₇ | C→33.4→I | 0.11 | 3.7 |
| 26 (Example 19) | n-C₃H₇ | C→37.6→N→60.4→I | 0.0889 | 12.6 |
| 27 (Example 20) | n-C₃H₇ | Sm→133.7→N→159.1→I | 0.106 | 1.23 |
| 28 (Example 21) | PFA | C→65.9→I | 0.103 | 0.9 |

C: solid phase
Sm: smectic phase
N: nematic phase
I: isotropic phase
PFA: —OCF₂CF=CF₂

FORMULATION EXAMPLE

Formulation examples of liquid crystal compositions containing the perfluoroallyloxy compounds of the present invention are shown in Tables 6 through 11. In Tables 6 to 11, CY stands for 1,4-cyclohexylene; PH, 1,4-phenylene; Pym, 5,2-pyrimidine; and Cn, a straight-chain alkyl group having n carbon atoms and, unless otherwise specified, bonded to the 4-position.

The liquid crystal compositions having the formulations of Tables 6 to 11 all had a low viscosity, a low refractive index anisotropy ($\Delta n$), a high dielectric anisotropy ($\Delta \epsilon$), and a high NI point (i.e., broad nematic phase range).

TABLE 6

| Liquid Crystal Compound | Compound No. | Amount (part by mass) |
|---|---|---|
| C5-CY-PH-OCF₂CF=CF₂ | No. 3 | 13 |
| C7-CY-PH-F | | 10 |
| C2-CY-CY-PH-OCF₃ | | 10 |
| C3-CY-CY-PH-OCF₃ | | 13 |
| C4-CY-CY-PH-OCF₃ | | 7 |
| C5-CY-CY-PH3F—OCF₂CF=CF₂ | No. 19 | 11 |
| C3-CY-CY-CH₂CH₂-PH-3,4-diF | | 10 |
| C5-CY-CY-CH₂CH₂-PH-3,4-diF | | 8 |
| C3-CY-CY-CH₂CH₂-PH-F | | 11 |
| C3-CY-PH-PH2F-CY-C3 | | 3 |
| C5-CY-PH-PH2F-CY-C3 | | 2 |
| C5-CY-PH-PH2F-CY-C5 | | 2 |

TABLE 7

| Liquid Crystal Compound | Compound No. | Amount (part by mass) |
|---|---|---|
| C2-CY-CY-PH3F—OCF₂CF=CF₂ | No. 19 | 13 |
| C3-CY-CY-PH3,4-diF | | 15 |
| C2-CY-PH-CN | | 12 |
| C3-CY-PH3,5-F—OCF₂CF=CF₂ | No. 16 | 10 |
| CH₃OCH₂-CY-PH-CN | | 6 |
| C2-PH-COO-PH-CN | | 6 |
| C2-Pym-PH-C2 | | 4 |
| C6-Pym-PH-OCF₂CF=CF₂ | No. 9 | 4 |
| C3-CY-CY-PH-CN | | 6 |
| C2-CY-CY-PH3F—CN | | 12 |
| C3-CY-CY-PH3F—CN | | 12 |

TABLE 8

| Liquid Crystal Compound | Compound No. | Amount (part by mass) |
|---|---|---|
| C3-CY-PH-CN | | 10 |
| C3-CY-PH3,5-diF—CN | | 10 |
| C2-PH-COO-PH3F—CN | | 2 |
| C3-PH-COO-PH3F—CN | | 3 |
| C5-CY-CY-CH=CH₂ | | 8 |
| CH₂=CH-CY-CY-PH-CH₃ | | 14.5 |
| C5-CY-CY-PH-OCF₂CF=CF₂ | No. 1 | 14 |
| C3-PH-C≡C-PH-OCF₂CF=CF₂ | No. 5 | 5 |
| C2-O-PH-C≡C-PH-CH₃ | | 5 |
| C3-O-PH-C≡C-PH-CH₃ | | 5 |
| C2-O-PH-C≡C-PH-F | | 4 |
| CH₂=CH-CY-PH-C≡C-PH-C2 | | 10 |
| CH₃CH=CH-CY-PH-C≡C-PH-C2 | | 9.5 |

TABLE 9

| Liquid Crystal Compound | Compound No. | Amount (part by mass) |
|---|---|---|
| C2-CY-CY-PH3,4-diF | | 8 |
| C3-CY-CY-PH3,4-diF | | 8 |
| C5-CY-CY-PH3F-OCF₂CF=CF₂ | No. 19 | 8 |
| C2-CY-PH-CN | | 8 |
| C3-CY-PH-CN | | 2 |
| C3-CY-PH-O-C2 | | 7 |
| C3-CY-PH-OCF₂CF=CF₂ | No. 3 | 7 |
| C3-CY-COO-PH-O-C2 | | 6 |
| CH₃OCH₂-CY-CY-C3 | | 5 |
| C2-CY-PH-CH₃ | | 6 |
| C3-CY-CY-PH-C3 | | 14 |
| C3-CY-CY-PH-OCH₃ | | 4 |
| C3-CY-CY-COO-PH-F | | 3 |
| C5-CY-CY-COO-PH-OCF₂CF=CF₂ | * | 3 |
| C3-CY-CY-PH-F | | 4 |

*Perfluoroallyloxy compound of the present invention

TABLE 10

| Liquid Crystal Compound | Compound No. | Amount (part by mass) |
|---|---|---|
| C3-CY-CY-C2 | | 10 |
| C3-CY-CY-C5 | | 10 |
| C7-CY-PH-F | | 5 |
| C3-CY-PH-C4 | | 9 |
| C3-CY-PH2,3-diF-OCF₂CF=CF₂ | * | 11 |
| C5-CY-PH2,3-diF—O-C2 | | 15 |
| C3-CY-CY-PH-di2,3-diF—OCF₂CF=CF₂ | No. 21 | 10 |
| C5-CY-CY-PH-2,3-diF—O-C2 | | 12 |
| C3-CY-CY-PH2,3-diF—CH₃ | | 7 |
| C5-CY-CY-PH2,3-diF—CH₃ | | 11 |

TABLE 11

| Liquid Crystal Compound | Compound No. | Amount (part by mass) |
|---|---|---|
| C3-CY3E-CY-C3 | | 5 |
| C3-CY-CY-CF$_3$ | | 5 |
| CH$_2$=CH-CY-CY-C5 | | 8 |
| C3-CY-PH-O—CF$_2$CF=CF$_2$ | No. 3 | 12 |
| C2-CY-CY-PH3F—O—CF$_2$CF=CF$_2$ | No. 19 | 11 |
| C3-CY-CY-PH3F—O—CF$_2$CF=CF$_2$ | No. 19 | 14 |
| C3-CY-CY-PH3,4-diF | | 13 |
| C3-CY-CY-PH3,5-diF—O—CF$_2$CF=CH$_2$ | No. 18 | 17 |
| C4-CY-CY-PH-CF$_2$H | | 10 |
| C2-CY-PH-PH-3,4,5-triF | | 5 |

INDUSTRIAL APPLICABILITY

The perfluoroallyloxy compound according to the present invention is useful as a liquid crystal material of a liquid crystal composition for an electro-optical display device of any display mode and any drive system.

What is claimed is:

1. A perfluoroallyloxy compound represented by general formula (I):

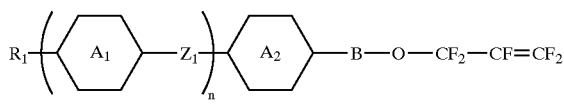

(I)

wherein $R_1$ represents R, RO, ROCO or RCOO; R represents an alkyl group which may have an unsaturated bond, a —CH$_2$— moiety of which may be displaced with —O—, —CO— or —COO—, and a part or all of the hydrogen atoms of which may be substituted with a halogen atom or a cyano group; $A_1$ and $A_2$ each represent 1,4-phenylene (a —CH= moiety of which may be displaced with —N=, and a part or all of the hydrogen atoms of which may be substituted with a halogen atom or a cyano group), 1,4-cyclohexylene (a —CH$_2$— moiety of which may be displaced with —O— or —S—, and a part or all of the hydrogen atoms of which may be substituted with a halogen atom or cyano group), 2,6-naphthylene or 2,6-decahydronaphthylene; $Z_1$ represents a single bond, —COO—, —OCO—, —CH$_2$CH$_2$—, —CH=CH—, —(CH$_2$)$_4$—, —CH$_2$O—, —OCH$_2$—, —(CH$_2$)$_3$O—, —O(CH$_2$)$_3$—, —CH=CHCH$_2$O—, —OCH$_2$CH=CH—, —C≡C—, —CF$_2$O— or —OCF$_2$—; B represents a single bond or alkylene group a part of the hydrogen atom of which may be substituted with a halogen atom or a cyano group; and n represents a number of 1 to 3; when n is 2 or 3, $A_1$'s and $Z_1$'s may each be the same or different.

2. The perfluoroallyloxy compound according to claim 1, wherein $R_1$ is an unsubstituted alkyl group or an unsubstituted alkenyl group.

3. The perfluoroallyloxy compound according to claim 1, wherein $R_1$ is —O—CF$_2$CF=CF$_2$.

4. The perfluoroallyloxy compound according to claim 1, wherein $A_1$ and $A_2$ are each an unsubstituted 1,4-phenylene group or an unsubstituted 1,4-cyclohexylene group.

5. The perfluoroallyloxy compound according to claim 1, wherein at least one of $A_1$ and $A_2$ is a 1,4-phenylene group substituted with one or two fluorine atoms.

6. The perfluoroallyloxy compound according to claim 1, wherein $Z_1$ is a single bond.

7. The perfluoroallyloxy compound according to any one of claim 1, wherein $Z_1$ is —CF$_2$O—.

8. A liquid crystal composition containing the perfluoroallyloxy compound according to claim 1.

9. An electro-optical display device having the liquid crystal composition according to claim 8 sealed in a liquid crystal cell thereof.

* * * * *